United States Patent [19]
Klopotek et al.

[11] Patent Number: 5,196,006
[45] Date of Patent: Mar. 23, 1993

[54] METHOD AND APPARATUS FOR EXCISION ENDPOINT CONTROL

[75] Inventors: Peter J. Klopotek; Alex C. Sacharoff, both of Framingham; Richard G. Caro, Boston, all of Mass.

[73] Assignee: Summit Technology, Inc., Waltham, Mass.

[21] Appl. No.: 773,781

[22] Filed: Oct. 10, 1991

Related U.S. Application Data

[63] Continuation of Ser. No. 343,038, Apr. 25, 1989, abandoned.

[51] Int. Cl.$^5$ ............................................. A61H 5/06
[52] U.S. Cl. ......................................... 606/12; 606/2; 606/4; 606/10; 128/897; 128/898
[58] Field of Search ............... 128/633, 664, 665, 395, 128/397, 398, 897, 898; 606/2, 4, 10–12

[56] References Cited

U.S. PATENT DOCUMENTS 4,504,727 3/1985 Melcher et al. ............... 219/121 LB
4,775,028 10/1988 de Heering ........................ 367/99
4,862,893 9/1989 Martinelli ....................... 128/662.03

OTHER PUBLICATIONS

"Laser Acoustic Measurements for Remotely Determining Bathymetry in Shallow, Turbid Waters", by Hickman et al.; J. Acoust. Soc. Am.; vol. 73, No. 3, Mar. 1983, pp. 840–843.

Webster's Third New International Dictionary, Philip Gove et al., ed., G & C Merriam Co., Springfield, Mass., 1965, p. 762.

Dyer et al., "Nanosecond Acoustic Studies on Ultraviolet Laser Ablation of Organic Polymers", Applied Physics Letters, vol. 48, pp. 445–447, Feb. 10, 1986.

Primary Examiner—David M. Shay
Attorney, Agent, or Firm—Thomas J. Engellenner

[57] ABSTRACT

Methods and apparatus for determining the depth of excision generated by a material removal process, for determining the thickness of unablated material below the excision or incision, and for providing endpoint control of a material removal process utilize acoustic transducers for measuring the time delay between a first acoustic pulse resulting from material removal and a second acoustic pulse reflected from a distal surface or boundary layer of the material. The time delay between the two pulses detected by the transducer provides a measure of excision depth and of the depth of material below the excision. Endpoint control is provided by terminating material removal when a selected excision depth is detected. The invention can be used, for example, as a real-time monitor of excision depth and residual lamella thickness under the excision during laser corneal surgery.

20 Claims, 5 Drawing Sheets

METHOD AND APPARATUS FOR EXCISION ENDPOINT CONTROL

This application is a continuation of application Ser. No. 343,038, filed Apr. 25, 1989 now abandoned.

BACKGROUND OF THE INVENTION

This invention concerns material removal systems and, more particularly, relates to apparatus and methods for determining the depth of excision generated by ablation, for determining the thickness of unablated material below the excision, and for providing automatic endpoint control of an ablation process. "Excision" is defined herein to include incisions and other cutting phenomena.

The utilization of lasers for material removal has become increasingly important for both commercial and industrial applications. In a variety of medical procedures, such as opthalmic surgery, a significant component of the procedure involves excision of a selected region or volume of tissue, in a minimally traumatic manner. One such technique is transverse excision ("T-excision") in which transverse cuts are made in the eye to modify a cylindrical curvature.

A critical aspect of the ablation procedure is measurement of excision depth, and determination of the endpoint of the excision procedure. In procedures such as radial keratotomy (RK), excisions may be as deep as 95% of the stroma. This depth must be precisely controlled to ensure predictable and reproducible results from the procedure, and to avoid damage to underlying material. In particular, in opthalmic surgical procedures such as T-excisions and RK, the depth of excision and the thickness of remaining tissue underlying the excision are parameters critical to the success of the procedure, and must be carefully controlled to minimize trauma and avoid perforation of the eye. Heretofore, there has been no reliable method or apparatus for accurately determining these dimensions.

It is known that when a focused energy device ablates material, the ablation products leave the material at high velocity. As a result of this event, an acoustic pulse is generated within the material. This acoustic pulse has a duration of comparable order of magnitude to that of the ablating laser pulse. The acoustic pulse propagates into the material, which may be, for example, a corneal structure, at the speed of sound, in a direction away from the ablation site where it is generated.

The detection of acoustic pulses resulting from laser ablation is discussed in Dyer, et al., "Nanosecond Acoustic Studies On Ultraviolet Laser Ablation Of Organic Polymers", *Applied Physics Letters*, Vol. 48, pp. 445–447, Feb. 10, 1986. This publication discusses the time evolution of ablative photodecomposition (APD), based on data generated by polyvinylidene fluoride (PVDF) piezoelectric transducers for sensing the acoustic pulses.

Moreover, it is known to provide acoustic feedback signals for controlling laser drilling. One such feedback loop is discussed in U.S. Pat. No. 4,504,727, Mar. 12, 1985, of Melcher, et al. The Melcher, et al. patent discloses the utilization of an acoustic sensor, such as a microphone or piezoelectric transducer, for sensing the initial pulses resulting from laser ablations. Endpoint detection is provided on the basis of differences in acoustic signal signatures between different layers, such as copper and epoxy-glass, in circuit boards.

Conventional systems such as those disclosed in these publications, however, cannot provide reliable measurement of the depth of excision or the remaining thickness of unablated material underneath the excision.

It is accordingly an object of the invention to provide methods and apparatus for determining the depth of excision generated by ablation.

It is another object of the invention to provide methods and apparatus for determining the thickness of unablated material below the excision.

It is a further object of the invention to provide methods and apparatus for endpoint control of an ablation process.

Other general and specific objects of the invention will in part be obvious and will in part appear hereinafter.

SUMMARY OF THE INVENTION

The present invention provides methods and apparatus for measuring the depth of an excision generated by a material removal process, and for measuring the residual thickness of substrate or material below the excision during the creation of an excision by the material removal process. One aspect of the invention involves sensing direct and reflected acoustic pulses resulting from laser ablation, and measuring the time delay between detected pulses.

The acoustic pulse generated by ablation propagates from its origin at the site of the excision. This direct pulse propagates through the material and can be detected by a transducer placed in contact with, or in close proximity to, the material in the vicinity of the excision. When the pulse reaches a distal surface or a boundary layer of the substrate or material, a portion of the pulse will be reflected. This reflected pulse propagates back through the material and can be detected by the transducer. The time delay between the two pulses detected by the transducer is a measure of excision depth and the thickness of the unablated substrate below the base of the excision.

Because this time delay is directly related to the thickness of the material at the excision point, the invention can provide, for example, real-time monitoring of excision depth and residual lamella thickness under the excision, during procedures such as corneal surgery, including photorefractive keratectomy (PRK), transverse-excisions (T-excisions) and radial keratotomy (RK); scleral incision procedures, such as glaucoma filtration surgery; corneal removal operations, such as transplants and the preparation of eyes for donor corneal implants; and other procedures based on laser ablation. This technique can also be extended to cover a wide variety of other procedures, medical and non-medical, where laser ablation is used to create an incision or excision in a section of substrate or material.

Another aspect of the invention involves sensing the ablation-generating energy pulse, such as a laser light pulse, sensing an acoustic pulse resulting from ablation, and measuring the time delay between the acoustic pulse and the ablation-generating energy pulse. This time delay provides a measure of excision depth.

The invention includes detection elements for detecting an initial acoustic pulse resulting from ablation, and a second acoustic pulse resulting from reflection of the initial pulse from a lower surface or inter-layer boundary of the material. This aspect of the invention also includes measuring elements for measuring a time delay between detection of the first acoustic pulse and detection of the second acoustic pulse, the time delay being representative of the depth of the incision. The detection elements can comprise an acoustic transducer, such as a commercially available polyvinylidene fluoride (PVDF), lead zirconate titinate (PZT), lead metaniobate, piezoelectric copolymers ($VF_2$ and $VF_3$), or other piezoelectric transducer elements.

Another aspect of the invention provides endpoint control of an excision process, utilizing controller elements responsive to the time delay measured by the measuring elements, for terminating the excision process when the time delay attains a selected value representative of a selected excision depth.

The invention also provides methods for monitoring the depth of an excision generated by ablation, and automatically controlling the endpoint of ablation. The method includes the steps of coupling an acoustic transducer to the material, detecting an initial acoustic pulse and a reflected acoustic pulse resulting from the ablation, measuring the time delay separating the first initial acoustic pulse and the reflected acoustic pulse, and terminating ablation when the time delay attains a selected value.

The invention will next be described in connection with certain illustrated embodiments; however, it should be clear to those skilled in the art that various modifications, additions and subtractions can be made without departing from the spirit or scope of the claims. For example, although the acoustic transducers of the present invention are illustrated as being coupled to the surface by means of a coupling agent such as an acoustic gel, it should be clear that various other arrangements for acoustic signal detection can be employed, including location of the sensor in proximity to the material undergoing ablation (without physical contact), implantation of the sensor into the material itself, or disposing arrays of sensors with the same or different sensing characteristics to detect the acoustic pulses generated by the ablation events.

BRIEF DESCRIPTION OF THE DRAWINGS

For a fuller understanding of the nature and objects of the invention, reference should be made to the following detailed description and the accompanying drawings, in which.

DESCRIPTION OF ILLUSTRATED EMBODIMENTS

Figures 1, 2:
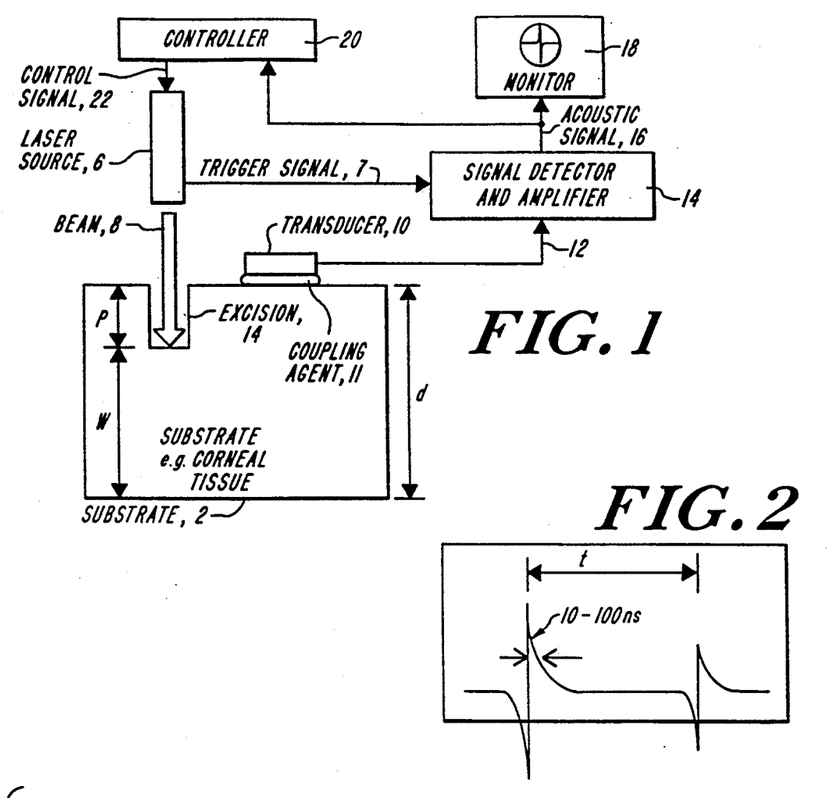
FIG. 1 is a block diagram depicting an apparatus for monitoring incision or excision depth in accordance with the invention.
FIG. 2 depicts schematic output waveforms generated by the apparatus of FIG. 1.

FIG. 1 is a schematic diagram depicting apparatus according to the invention, for measuring the depth of excisions generated by laser ablation of a material, such as corneal tissue; for measuring the thickness of unablated material beneath the excision; and for endpoint control of laser ablation. "Excision" is defined herein to include incision and other cutting and material removal procedures. In addition, other energy sources may be utilized in place of a laser for material removal, including ion beam sources, electron beams, ultrasound, and water jets.

The apparatus depicted in FIG. 1 includes a laser source 6, such as a conventional argon fluoride UV excimer laser, for generating a beam 8 capable of generating an excision 4, through ablation of the substrate 2. The substrate 2 may be, for example, corneal tissue. When beam 8 causes ablation of the substrate 2, an acoustic pulse is generated, as a result of ablation products escaping the material at high velocity. Subsequently, a second acoustic pulse is reflected from the surface or boundary beneath the excision—i.e., the lower surface of substrate 2. Each of these acoustic Pulses can be detected by an acoustic transducer 10. The transducer 10 can be constructed, for example, from conventional PVDF or PZT piezoelectric transducer elements, as discussed in detail hereinafter in connection with FIGS. 6–10.

Referring again to FIG. 1, the transducer output signal 12 generated by transducer 10 is fed to a signal detector and amplifier module 14, which amplifies and processes the transducer output signal 12 to provide an amplified signal 16. Signal detector and amplifier module 14 can be designed and constructed in accordance with known engineering practice, as discussed in greater detail below in connection with FIG. 3. The amplified signal 16 at the output of signal detector and amplifier module 14 can be displayed on a display device 18, such as an oscilloscope, monitor or other CRT device. Alternatively, the amplified signal 16 can be transmitted to a controller 20 to provide feedback control of the laser source 6 for automatic endpoint control of laser ablation. A method of automatic endpoint control by measurement of return pulses, which can be implemented by controller 20, is described in greater detail below.

Excision depth, and the thickness of unablated material beneath the excision, are determined, in accordance with the invention, as a function of the time separation between detection of the first pulse resulting from ablation and detection of the return or reflected pulse. In particular, if V = the speed of sound in the material,
W = the thickness of unablated material beneath the excision or incision,
P = the depth of the excision or incision,
D = the total thickness of the material,
and if the angle subtended by the centerline of the excision base and the center of the transducer is small, then the time delay between the first and second acoustic pulse incident on the transducer is given by $$T = 2W/V \tag{1}$$

When the excision is first initiated, P=0, and W=D. Thus, for the initial few ablating pulses, $$T_1 = 2D/V \tag{2}$$

Subsequently, the transducer measures $$T_2 = 2W/V \tag{3}$$

for a certain excision depth. Because $$T_2/T_1 = W/D \tag{4}$$

it is possible to determine when a selected percentage excision depth has been attained, independent of knowledge of either D or V. Moreover, it is also possible to determine when a selected depth P has been attained, simply by knowing the total thickness of the substrate, D.

The formulae set forth above can be utilized, with appropriate geometrical correction factors, to describe the case of larger subtended angles between the excision center line and the transducer. Those skilled in the art will appreciate that both W and P can be determined from these measurements. In accordance with the invention, these values can be determined without a knowledge of propagation velocity V. The elimination of the necessity for knowledge of V removes a traditional source of inaccuracy in this type of measurement technique. Moreover, the total initial thickness, D, can be measured in a variety of ways. For example, for "in-vivo" corneal thickness measurements, optical or ultrasound pachymetry can be readily utilized.

The invention is advantageously practiced in connection with excision procedures in which the angle between the energy source and the transducer is small, such as in RK or transverse excision (T-excision) procedures, and can also be utilized in connection with other laser ablation surgical procedures and industrial material removal procedures utilizing a variety of energy sources.

In a preferred practice of the invention depicted in FIG. 1, laser source 6 is an argon fluoride excimer laser which is activated to generate a beam 8 having uniform energy density and a wavelength of approximately 193 nanometers. This beam is directed onto the eye with beam dimensions comparable to that of the desired excision. Typical beam dimensions are 1×5 millimeters, 2×0.8 millimeters, or 0.15×4 millimeters. The beam preferably has an energy density of between approximately 100 and approximately 1,000 millijoules per square centimeter, and the laser 6 can be operated at a various pulse rates typically ranging from approximately 1 Hz to approximately 20 Hz.

The transducer 10 is mounted and coupled to the substrate 2, such as a human eye, typically with a coupling agent 11, which can be, for example, an acoustically transmissive solid, liquid or gel. The transducer 10 can be mounted to the eye as a free-standing monitoring device, or as a part of a rigid support stage which serves to immobilize the eye during the ablation procedure. A preferred mounting technique is described below in connection with FIG. 6. Preferably, transducer 10 has a rapid time response, on the order of ten nanoseconds. Examples of rapid time response acoustic transducers include commercially available PVDF or other piezoelectric transducers. The transducer output signal 12 can then be amplified and processed by amplifier module 14 and the amplified signal 16 displayed on a display device 18.

Acoustic signals resulting from laser ablation of a substrate are schematically illustrated in FIG. 2. The horizontal axis represents time T, while the vertical axis represents signal amplitude. The first signal peak represents the initial pulse created by the ablation event, while the second, lower amplitude pulse represents the pulse reflected from a surface or inter-layer boundary beneath the excision. The width of the initial, high amplitude pulse is typically 10–100 nanoseconds, as indicated in FIG. 2. Moreover, the time separation of the two pulses on the display, $$T = 2W/V \tag{1}$$

provides a direct measure of excision depth, as described above. As the excision deepens with consecutive laser pulses, the spacing T=2W/V of the two peaks in FIG. 2 decreases, and approaches a predetermined limiting value representative of the desired excision depth.

The invention can be advantageously practiced in connection with a feedback control loop including a controller 20 shown in FIG. 1. Controller 20 can be a conventional microprocessor, computer, or the like, which receives time delay information from the signal detector 14, and which generates control signals 22 for controlling the output of laser source 6 illustrated in FIG. 1. In particular, when the detected time delay reaches a predetermined limiting value, indicating that a desired excision depth P or residual substrate depth W has been attained, the controller 20 can terminate laser ablation. The controller 20 can also be configured to accept user input data representing a desired value of P or W.

Figure 3:
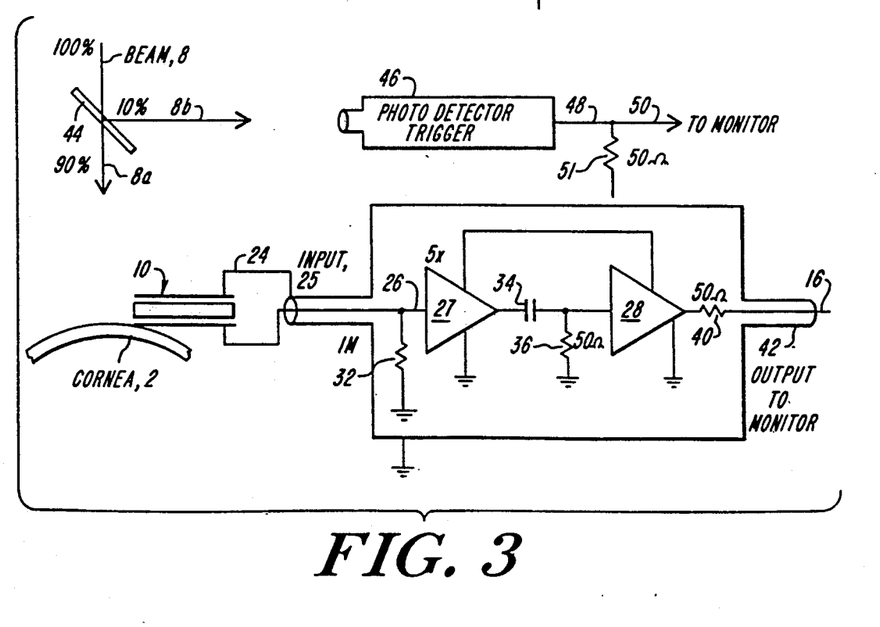
FIG. 3 is a schematic diagram giving detail of the detection and amplifying elements of FIG. 1.

FIG. 3 illustrates signal acquisition elements utilized in accordance with the invention. Beam 8, generated by the laser source illustrated in FIG. 1, impinges upon a conventional beam splitter 44, which transmits beam 8a toward the substrate (cornea 2), and reflects beam 8b toward a photodetector trigger 46 discussed in detail below. Beam 8a preferably comprises at least ninety percent of the energy of beam 8, while beam 8b represents ten percent or less of the energy of beam 8.

The illustrated transducer 10 can be formed, for example, from a PVDF sheet, approximately 9 μm in thickness. This thickness is non-critical, and can be varied in accordance with specific requirements. The transducer 10 is coupled to the cornea 2 and responds to acoustic signals, in a known manner, to generate electrical signals during laser ablation of the cornea. The signals 12 generated by transducer 10 are conducted to the input 25 of detection and amplification block 14 by cable 24. Cable 24 can include a length of two-conductor shielded cable. The signals 12 are conducted from block input 25 to input 26 of an FET preamplifier module 27, and input 26 can be coupled to ground by a 1 megohm resistor 32. A suitable FET preamplifier is type AH0013, having a nominal gain of 5, commercially available from OEI Corporation, Tucson, Ariz.

The amplified signal from module 27 can be filtered by a capacitor 34 and fed to the input of non-inverting amplifier module 28, which can be coupled to ground by a 50 ohm resistor 36. The amplifier module 28 can be a type CLC300A, having a nominal gain of 16, commercially available from ComLinear Corporation, Fort Collins, Colo. The output of the non-inverting amplifier module 28 is conducted through a 50 ohm resistor 40 to a coupling 42 adapted for connecting the amplified signal 16 to a controller and a display device (illustrated in FIG. 1), which can be a storage or digital oscilloscope for real-time monitoring of the ablation process. A preferred oscilloscope is the Model 2432 digital storage oscilloscope commercially available from Tektronics Corporation, Beaverton, Oreg. The oscilloscope can be triggered by a conventional photodetector trigger circuit 46, which generates a trigger signal 48 in response to beam component 8b. The output signal 48 can be conducted to an oscilloscope along output line 50, which is coupled to ground by a 50 ohm resistor 51.

The circuit illustrated in FIG. 3 thus provides a photodetector trigger 46 for detecting the laser pulse, and a transducer 10 and detection module 14 for detecting acoustic pulses resulting from laser ablation of the substrate. The circuit can therefore be utilized to calculate excision depth in any of three modes. In particular, the acoustic detector elements of the circuit can be used to measure the time delay between an initial acoustic pulse resulting from ablation, and a second acoustic pulse reflected from a boundary layer of material beneath the excision. Alternatively, the optical and acoustic detection elements of the circuit can measure a time separation between the laser light pulse and the acoustic pulse reflected from a boundary layer beneath the excision area. The circuit can further be utilized to measure the difference in time separations between the laser emission and detection of the initial and reflected acoustic pulses. Excision depth can be calculated, based on these time delay measurements, by utilizing Equation 1 above, which relates excision depth to time delay. This relationship between time delay and excision depth is graphically illustrated in FIGS. 4A, 4B, 5A and 5B, which depict acoustic and electrical signals generated by the apparatus illustrated in FIG. 3 during laser ablation.

Figures 4A, 4B, 5A, 5B:
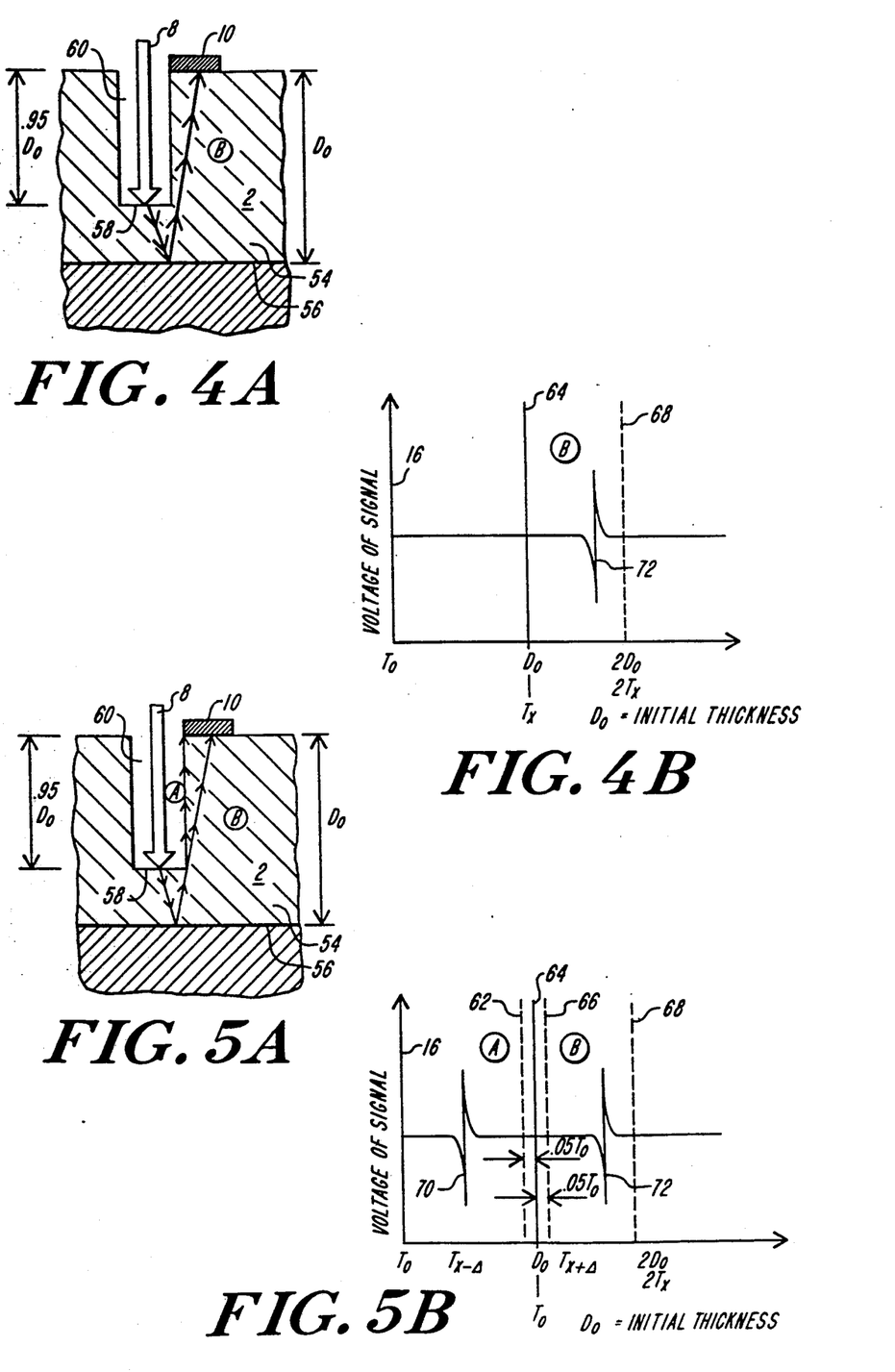
FIG. 4A depicts the propagation path of a reflected acoustic signal generated during laser ablation.
FIG. 4B depicts a simplified waveform produced at the output of the circuit of FIG. 3 in response to the acoustic signal depicted in FIG. 4A.
FIG. 5A depicts propagation paths of initial and reflected acoustic signals generated during laser ablation.
FIG. 5B depicts simplified waveforms produced at the output of the circuit of FIG. 3 in response to the acoustic signals depicted in FIG. 5A.

FIG. 4A shows the propagation path of an acoustic echo signal generated during laser ablation of a layer 54 of a material 2. The material 2 can be, for example, an eye, and the layer 54 can be a cornea. The cornea 54 has a lower boundary 56 defining a thickness or depth $D_0$. Boundary 56 in this example can be the interface between cornea and aqueous humor in the human eye. Laser beam 8, directed upon the cornea 54, causes ablation of tissue, thereby generating an acoustic signal which propagates along path B illustrated in FIG. 4A. In particular, the acoustic pulse is initiated at the base 58 of the excision 60 and reflected from the boundary 56 of the cornea 54, propagating along path B. This acoustic signal is detected by transducer 10, which can be coupled to the upper surface of material 2 in a manner described above in connection with FIG. 1. In response to this reflected acoustic pulse, transducer 10 produces an output signal that is amplified by the circuit illustrated in FIG. 3 to produce the waveform depicted in FIG. 4B.

FIG. 4B shows a time/voltage graph of the output signal 16 of the circuit illustrated in FIG. 3, corresponding to the reflected acoustic signal graph represents time T, measured from time $T_0$—i.e., the time at which the laser pulse is detected by the photodetector depicted in FIG. 3. The vertical axis of the graph represents signal voltage. Referring now to both FIGS. 4A and 4B, signal peak 72 corresponds to the acoustic echo pulse which was reflected from the boundary 56 beneath the ablation site 60, along path B. The horizontal, or time-axis, position of signal peak 72 is accordingly related to the path length and corresponding acoustic transit times along path B, which in turn is a function of excision depth.

Prior to the initiation of ablation, the length of path B is approximately $2D_0$—twice the thickness of cornea 54. Accordingly, signal peak 72, which corresponds to the signal propagated along path B, is initially at time $2T_x$, designated in FIG. 4B by dashed vertical line 68. As the ablation procedure progresses and the depth of excision 60 increases, the length and acoustic signal transit time along path B decrease, and signal peak 72 moves to the left. The embodiment of FIGS. 4A and 4B accordingly measures the acoustic transit time along path B, and calculates excision depth as a function of transit time.

As discussed above, however, the circuit illustrated in FIG. 3 can also be utilized to measure transit time differences between initial and reflected acoustic pulses, thereby providing another measure of excision depth. Measurement of transit time differences is illustrated in FIGS. 5A and 5B.

FIG. 5A shows the propagation paths of initial and reflected acoustic signals generated during laser ablation of a cornea 54 in an eye 2. The cornea 54 has a lower boundary 56 defining a thickness or depth $D_0$. Laser beam 8, directed upon the cornea 54, causes ablation of tissue, thereby generating acoustic signals which propagate along paths A and B illustrated in FIG. 5A. In particular, a first acoustic pulse is initiated at the base 58 of the excision 60, propagating along path A. This acoustic signal is detected by piezoelectric transducer 10, which can be coupled to the upper surface of material 2 in a manner described above in connection with FIG. 1. The ablation also resul s in an "echo," or second acoustic pulse initiated at the base 58 and reflected from the boundary 56 of the cornea 54, propagating along path B. This second acoustic signal is also detected by transducer 10, which responds to these first and second pulses by producing an output signal that is amplified by the circuit illustrated in FIG. 3 to produce the waveform depicted in FIG. 5B.

FIG. 5B shows a time/voltage graph of the output signal 16 of the circuit illustrated in FIG. 3, corresponding to the acoustic signals illustrated in FIG. 5A. The horizontal axis of the graph represents time T, measured from time $T_0$—i.e., the time at which the laser pulse is detected by the photodetector depicted in FIG. 3. The vertical axis of the graph represents signal voltage. Referring now to both FIGS. 5A and 5B, signal peak 70 represents the response to the acoustic pulse which propagated along path A, while signal peak 72 corresponds to the acoustic echo pulse which was reflected from the boundary 56 beneath the ablation site 60, along path B. The horizontal, or time-axis, Positions of signal peaks 70 and 72 are accordingly related to the path lengths, and corresponding acoustic signal transit times, along paths A and B, which in turn are a function of excision depth.

At the initiation of ablation, the depth component of path A is approximately zero, with a known displacement, d, between the transducer 10 and the excision site, and the length of path B is approximately $2D_0$—twice the thickness of cornea 54. Accordingly, signal peak 70, which corresponds to the signal propagated along path A, is initially at time $[T_o + d/V]$, and signal peak 72, which corresponds to the signal propagated along path B, is initially at time $2T_x$, designated in FIG. 5B by dashed vertical line 68.

Still referring to FIGS. 5A and 5B, as the ablation procedure progresses and the depth of excision 60 increases, the length and acoustic signal transit time along path A increase, while the length and acoustic signal transit time along path B decrease. Signal peak 70 is displaced to the right, while signal peak 72 moves to the left. When excision depth is equal to the thickness $D_0$ of cornea 54, the respective path lengths and acoustic signal transit times along paths A and B are approximately equal. Thus, when the excision reaches the boundary 56 of cornea 54, signal peaks 70 and 72 are both located at approximately time $T_x$, designated in FIG. 5B by vertical line 64.

The efficacy of T-excision and RK procedures is closely related to excision depth. Optimum excision depth is approximately 95% of corneal depth, so that each excision approaches, but does not result in, perforation of the cornea. Thus, in a preferred practice of the invention, signals representative of excision depth are generated by the circuitry depicted in FIG. 3 and fed to controller 20 indicated in FIG. 1, for terminating laser ablation at a selected excision depth less than $D_0$ (typically $0.95\ D_0$). This endpoint control of laser ablation is implemented by utilizing the circuitry depicted in FIG. 3 for detecting signal peaks 70 and 72 shown in FIG. 5B, measuring the time delay separating each Peak from the laser trigger event ($T_0$), and comparing the observed time delay to a calculated time delay corresponding to a selected or excision depth. Thus, for example, ablation can be terminated when signal peaks 70 and 72 reach time-axis positions $(T_x - \Delta)$ and $(T_x + \Delta)$, respectively, where $\Delta$ corresponds to a depth of $0.05\ D_0$. These signal peak locations, indicated in FIG. 5B by dashed lines 62 and 66, respectively, correspond to an excision depth of $0.95\ D_0$.

Figure 6:
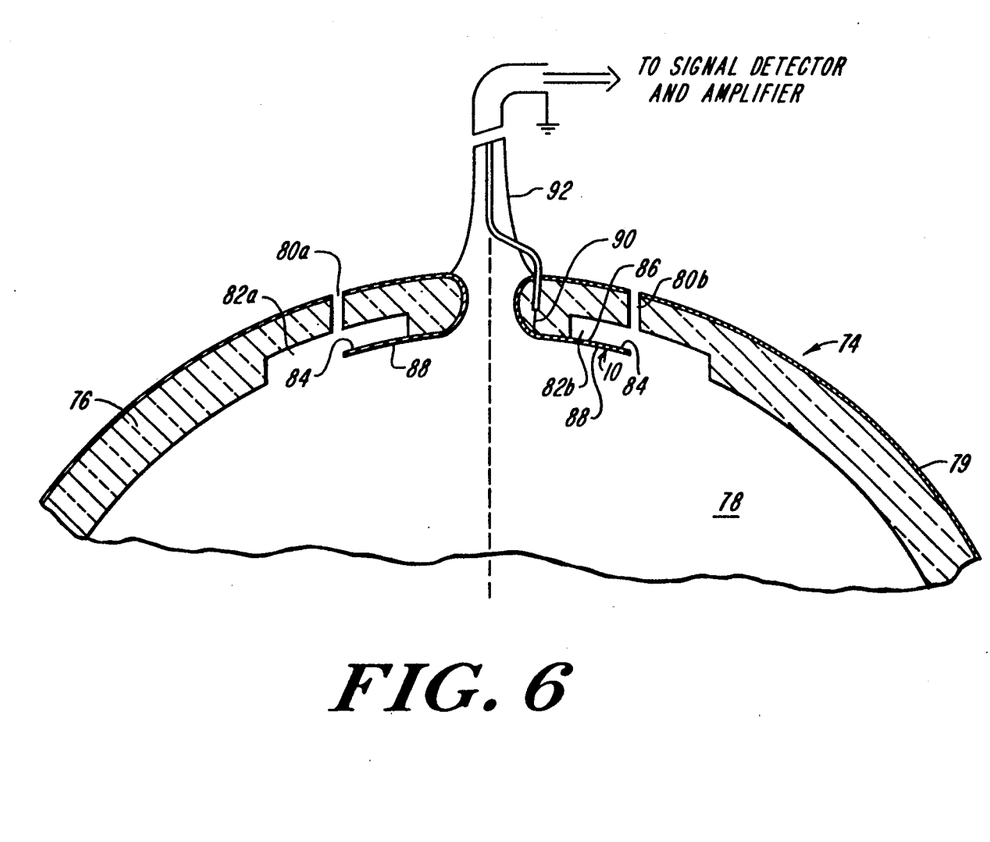
FIG. 6 is a side view of a transducer configuration utilized in accordance with the invention.

Depth monitoring and endpoint control of laser ablation can be advantageously practiced in connection with the transducer assembly depicted in FIG. 6. The transducer assembly 74 shown in FIG. 6 utilizes a contact lens 76 assembly constructed, for example, from conventional polymethylmethacrylate (PMMA) film and coupled to the eye 78. The contact lens assembly 76 acts as a mounting structure to which the inner surface of transducer module 10 is bonded, and serves as an optical mask for defining the ablation targets on the eye 78. In particular, the contact lens structure 76 includes two slits 80a and 80b for permitting laser light or other energy to impinge upon selected target areas on the eye 78. The contact lens structure 76 also incorporates air baffles 82a and 82b for blocking the acoustic response of the outer surface of the transducer module 10, so that the transducer module 10 detects only those acoustic signals propagating within the eye 78.

The transducer module 10 consists of a PVDF film 84 approximately 9 μm thick, for example, to which upper and lower conductive layers 86, 88 are bonded. The conductive layers can be formed from nickel-silver conductive patterns approximately 500 angstroms thick. The upper conductive layer 86, bonded to the outer surface of the PVDF film 84, serves as an upper electrode, while the lower conductive layer 88, bonded to the inner surface of the PVDF film 84, acts as a ground plane. PVDF film 84 responds to ablation-generated acoustic signals in a known manner, generating a voltage difference between upper electrode 86 and ground plane 88. The electrodes can be configured as either strip electrodes or dot electrodes, as discussed in detail hereinafter. Preferred dimensions for strip electrodes and dot electrodes, respectively, are 100 μm × 4 mm and 100 μm × 100 μm. Solder connections can be made to the electrode 86 and ground plane 88 surrounding the PVDF film 84, and a coaxial cable 92 including conductor 90 can be used to lead voltage signals to the preamplifier elements depicted in FIG. 3.

Figure 7:
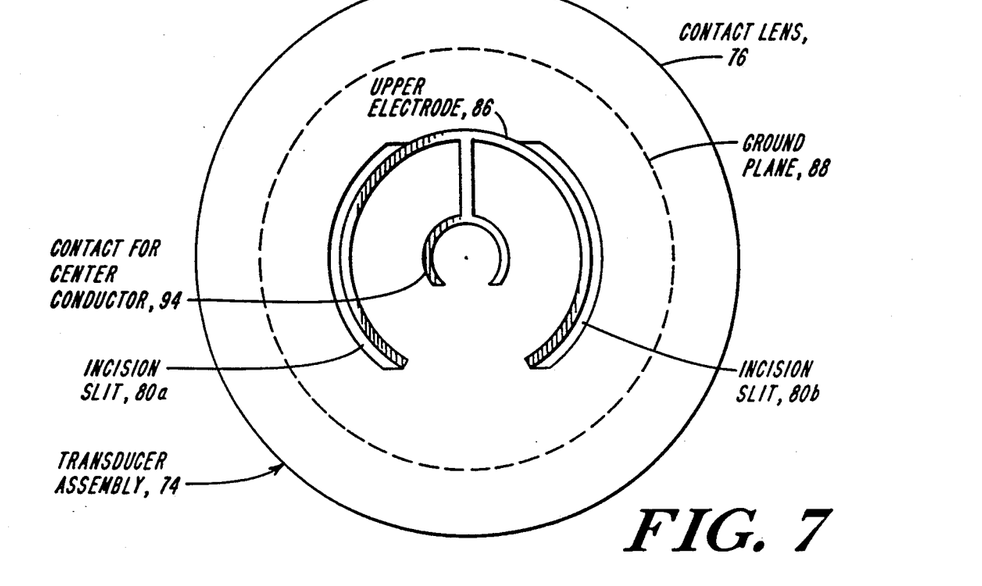
FIG. 7 is a top view of the transducer configuration of FIG. 6.

FIG. 7 is a top view of the transducer configuration 74 of FIG. 6, showing contact lens structure 76, having slits 80a and 80b disposed on opposite sides of the electrode pattern 86, for passing UV light to selected arcuate excision areas during RK and T-excision procedures. The electrode pattern 86 is substantially circular, substantially conforming to the radius of excision. The ground plane 88, which is bonded to the lower surface of the PVDF film 84, is illustrated in phantom.

Figure 8:
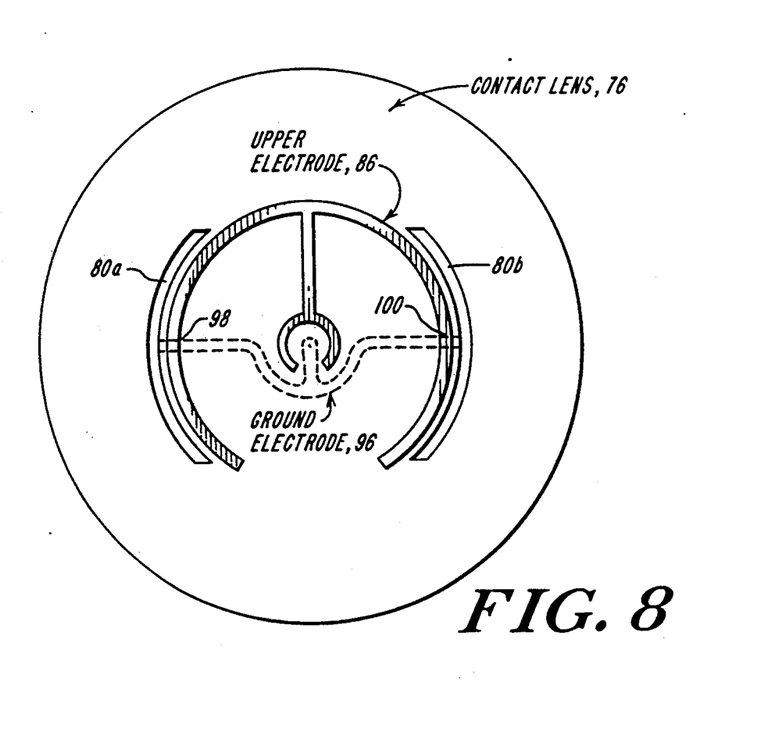
FIG. 8 is a top view of a localized sensor configuration in accordance with the invention.

The transducer depicted in FIGS. 6 and 7 is sensitive to acoustic ablation signals propagating throughout the area covered by the electrode 86. Certain laser ablation procedures, however, are more readily monitored by a transducer structure having localized sensitivity FIG. 8 depicts an example of such a transducer structure. The electrode pattern is similar to that shown in FIG. 7, but the ground electrode 96 is reduced to a roughly U-shaped configuration which underlies the upper electrode 86 at only two regions 98 and 100, located adjacent to the midpoints of slits 80a and 80b, respectively. This configuration yields a transducer assembly which responds only to acoustic signals propagating through the active regions bounded by the overlap areas of ground electrode 96 and upper electrode 86.

Figure 9:
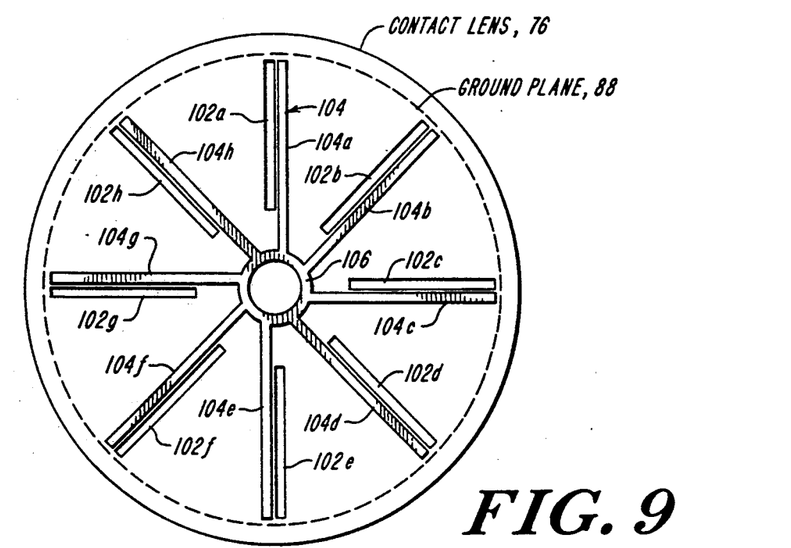
FIG. 9 is a top view of a radial electrode configuration in accordance with the invention.

Certain laser ablation procedures, such as RK, require that multiple radial excisions be formed in the cornea. FIG. 9 shows a transducer electrode configuration adapted for monitoring excision depth during such procedures. The PVDF contact lens assembly 76 has eight radial slits 102a-102h, for defining RK target areas for UV laser light ablation. The upper electrode 104 includes eight conductive radial arms 104a-104h, each located adjacent to a respective slit 102a-102h, and a central circular conductor region 106 linking the arms of the spyder. Each conductive arm can be approximately 4 mm × 0.15 mm. The ground plane, indicated by dashed line 88, underlies the entire upper electrode 104, thus providing eight active transducer "strips" within which acoustic signals can be detected.

Figure 10:
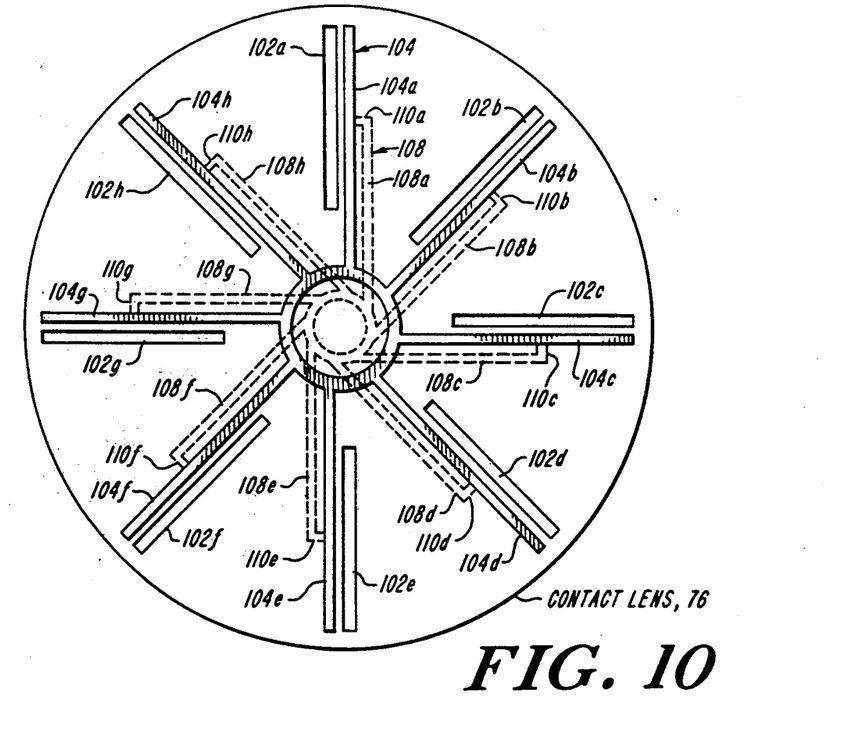
FIG. 10 is a top view of a localized radial sensor electrode configuration also in accordance with the invention.

FIG. 10 shows another transducer configuration, in accordance with the invention, which provides localized sensitivity to acoustic signals. This structure utilizes a contact lens assembly 76 and upper electrode 104 similar to those depicted in FIG. 9. The ground electrode 108, however, is reduced to a spyder configuration having eight arms 108a-108h, each offset from upper electrode arms 104a-104h and underlying the upper electrode arms only at selected regions 110a-110h. These overlap regions, which can be approximately 100 μm × 100 μm in area, define active regions in which ablation-generated acoustic signals are detected.

Those skilled in the art will appreciate that transducer and electrode configurations other than those depicted in FIGS. 6-10 may be utilized for monitoring and endpoint control of other surgical or industrial material removal procedures, such as ablation by lasers, charged particle beams, or water jets, and are within the scope of the invention.

It will thus be seen that the invention efficiently attains the objects set forth above, among those made apparent from the preceding description. In particular, the invention provides methods and apparatus for determining the depth of excision or incision generated by laser ablation, for determining the thickness of unablated material below the excision or incision, and for providing endpoint control of a laser ablation process.

It will be understood that changes may be made in the above construction and in the foregoing sequences of operation without departing from the scope of the invention. For example, a transducer constructed in accordance with the invention can be implanted into the material to be ablated, and more than one transducer can be utilized, so as to provide localizing registration signals. The transducers can be of the acousto-optical type. Moreover, the transducer elements can be adapted for incorporation into a catheter, and used for monitoring cutting depth in arterial cleaning procedures. It is accordingly intended that all matter contained in the above description or shown in the accompanying drawings be interpreted as illustrative rather than in a limiting sense.

Having described the invention, what is claimed as new and secured by Letters Patent is:

1. Apparatus for measuring, in a biological material, the depth of an excision generated in the biological material and caused by a laser ablation process, the apparatus comprising
   detection means for detecting an acoustic pulse generated by the laser ablative process, and for detecting a second acoustic pulse resulting from the first acoustic pulse, said second acoustic pulse being reflected from a boundary of the material, said detection means being located such that
   said first acoustic pulse travels along a first acoustic path to said detection means and said second acoustic pulse travels along a second acoustic path to said detection means, and such that
   the length of the second acoustic path is greater than the length of the first acoustic path, and
   measuring means for measuring a time separation between detection of the first acoustic pulse and detection of the second acoustic pulse, said time separation being representative of excision depth.

2. Apparatus according to claim 1, further including controller means responsive to said time separation, for determining the laser ablative process when said time separation attains a selected value.

3. Apparatus according to claim 1, wherein said detection means includes an acoustic transducer.

4. Apparatus according to claim 3, wherein said acoustic transducer includes a polyvinylidene fluoride piezoelectric transducer element.

5. Apparatus according to claim 1, wherein the laser ablation process is corneal surgery, and wherein the apparatus further comprises photodetector means for detecting an ablative laser light emission substantially simultaneous with the laser light emission, and wherein said measuring means includes means responsive to detection of laser light emission, for measuring a first time separation between the laser light emission and detection of the first acoustic pulse, and a second time separation between the laser light emission and detection of the second acoustic pulse, the difference between said first time separation and said second time separation being representative of excision depth.

6. Apparatus according to claim 5, further including controller means responsive to said difference, for terminating ablation when said difference attains a selected value.

7. Apparatus for measuring, in a biological material, the depth of an excision generated in the biological material and caused by laser ablation, the apparatus comprising
   photodetector means for detecting an ablative laser light emission, the detection being substantially simultaneous with the laser light emission,
   acoustic detection means for detecting an acoustic pulse resulting from the ablation, said acoustic pulse traveling through the material for a finite time and being reflected from a boundary of the material, and
   measuring means for measuring a time separation between detection of the laser light emission and detection of the acoustic pulse, said time separation being representative of excision depth.

8. Apparatus according to claim 7, further including controller means responsive to said time separation, for terminating ablation when said time separation attains a selected value.

9. Apparatus according to claim 7, wherein said acoustic detection means includes an acoustic transducer.

10. Apparatus according to claim 9, wherein said acoustic transducer includes a polyvinylidene fluoride piezoelectric transducer element.

11. A method for measuring, in a biological material, the depth of an excision in the biological material generated by laser ablation at an ablation site, the method comprising the steps of
    detecting an acoustic pulse generated by the ablation and propagating from the ablation site to the detection site along a first acoustic path, the first acoustic path including the ablation site and the detection site and having a first acoustic path length,
    detecting, at the detection site, a second acoustic pulse resulting from the first acoustic pulse, said second acoustic pulse being reflected from a boundary of the material and propagating to the detection site along a second acoustic path, the second acoustic path including the boundary and the detection site and having a second acoustic path length greater than the first acoustic path length, and
    measuring a time separation between detection of the first acoustic pulse and detection of the second acoustic pulse, said time separation being representative of excision depth.

12. A method according to claim 11, further comprising the step of terminating ablation when said time separation attains a selected value.

13. A method according to claim 11, wherein said detecting steps include the step of utilizing an acoustic transducer.

14. A method according to claim 13, wherein the step of utilizing an acoustic transducer includes the step of constructing the transducer from a polyvinylidene fluoride piezoelectric transducer element.

15. A method according to claim 11, the method further including the steps of
    detecting a laser light emission substantially simultaneously with the laser light emission, measuring a first time separation between the laser light emission and detection of the first acoustic pulse, and measuring a second time separation between the laser light emission and detection of the second acoustic pulse, the difference between said first time separation and said second time separation being representative of excision depth.

16. A method according to claim 15, further including the step of terminating ablation when said difference attains a selected value.

17. A method for measuring, in a corneal surgical procedure, the depth of an excision generated in the cornea through laser ablation, the method comprising the steps of detecting a laser light emission substantially simultaneously with the laser light emission, detecting an acoustic pulse resulting from the ablation, said acoustic pulse traveling through the cornea for a finite time and being reflected from a boundary of the cornea, and measuring a time separation between detection of the laser light emission and detection of the acoustic pulse, said time separation being representative of excision depth.

18. A method according to claim 17, further including the step of terminating ablation when said time separation attains a selected value.

19. A method according to claim 17, wherein said detecting step includes the step of utilizing an acoustic transducer.

20. A method according to claim 19, wherein the step of utilizing an acoustic transducer includes the step of constructing the transducer from a polyvinylidene fluoride piezoelectric transducer element.

* * * * *